United States Patent [19]

Alsoe et al.

[11] Patent Number: 5,378,811
[45] Date of Patent: Jan. 3, 1995

[54] PURE C3B INACTIVATOR AND A PROCESS FOR PRODUCING SAID PROTEIN

[75] Inventors: Karina O. Alsoe, Copenhagen K; Jesper Kihl, Lyngby, both of Denmark

[73] Assignee: Novo Nordisk A/S, Bagsvaerd, Denmark

[21] Appl. No.: 89,905

[22] PCT Filed: Dec. 19, 1989

[86] PCT No.: PCT/DK89/00297
§ 371 Date: May 21, 1991
§ 102(e) Date: May 21, 1991

[87] PCT Pub. No.: WO90/06759
PCT Pub. Date: Jun. 28, 1990

Related U.S. Application Data

[63] Continuation of Ser. No. 689,751, May 21, 1991, abandoned.

[30] Foreign Application Priority Data

Dec. 20, 1988 [DK] Denmark .............................. 7084/88

[51] Int. Cl.⁶ ..................... A61K 35/16; A61K 37/02; A61K 37/06; C07G 7/00
[52] U.S. Cl. .................... 530/381; 530/384
[58] Field of Search ................................ 530/381, 384

[56] References Cited

U.S. PATENT DOCUMENTS 4,440,679  4/1984  Fernandes et al. ................. 530/381
4,623,717  11/1991  Fernandez et al. ................ 530/382

FOREIGN PATENT DOCUMENTS 0222611  11/1986  European Pat. Off. .

OTHER PUBLICATIONS

Seya and Nagasawa, 1988, J. Biochem. 103:792–796.
Ziegler et al., 1975, J. Clin. Investig. 55:668–672.
Rasmussen et al., 1988, Clin. exp. Immunol. 74:131–136.
Barrett and Boyle, 1984, J. Pediatr. 104:76.

Primary Examiner—Howard E. Schain
Assistant Examiner—P. Lynn Touzeau
Attorney, Agent, or Firm—Steve T. Zelson; Cheryl H. Agris

[57] ABSTRACT

A pure Factor I protein essentially free of infectious virus. Factor B and C3. The protein is derived from plasma and pasteurized by heating to a temperature of 50° to 65° C. for 0.5 to 100 hours in the presence of one or more stabilizers for Factor 1. Preparations containing the protein are useful in the treatment of Factor I deficiency and autoimmune diseases.

4 Claims, No Drawings

PURE C3B INACTIVATOR AND A PROCESS FOR PRODUCING SAID PROTEIN

This application is a continuation application of copending application Ser. No. 07/689,751 filed May 21, 1991, now abandoned.

The invention relates to a pure Factor I protein, essentially free of infectious virus, Factor B and C3. The invention also relates to an injectable preparation containing the pure Factor I protein, and derived from plasma. Such a preparation may be used in the treatment of Factor I deficiency and in the treatment of autoimmune diseases. The invention also relates to a process for producing the pure factor I protein, recovered from plasma.

The complement system is an enzyme cascade system consisting of more than 20 plasma proteins. The system is important in the defence against microbial infections. It is activated partly by antigen antibody complexes via the classical pathway, partly by e.g. bacterial membranes and soluble substances via the alternative pathway. In both situations, the activation leads to formation of some active enzyme complexes, C3 covertases, having the central component C3 as a substrate. The C3 protein is cleaved in a small fragment, C3a, and in a larger fragment, C3b. C3b forms part of the C3 convertase of the alternative pathway. Thus, an amplification principle of the alternative pathway of the complement system is incorporated. The C3 convertase of the alternative pathway also includes a Factor Bb, a degradation product from the complement factor, Factor B.

The system is regulated by several proteins which inhibit the activated enzyme complexes. Factor I (C3b inactivator or KAF is such a regulator protein since it enzymatically degrades the C3b fragment to an intermediate fragment iC3b and further to C3c and C3d.

Factor I deficiency entails that C3b cannot be degraded to smaller cleavage products. This results in a continuous and uncontrolled formation of the alternative C3 convertase, with a consequent reduction or depletion of proteins from the alternative pathway. This involves less resistance to certain types of infections. Thus, increased frequency of e.g. cerebrospinal menigitis and pneumonia has been reported in Factor I deficient patients, cf. S. C. Ross et al., Medicine (1984) 63(5), 243.

Treatment with intravenous infusion of Factor I preparation, purified from plasma, has been described, cf. J. B. Ziegler et al., J. Clin. Invest. (1975) 55,668. This treatment has been found to be effective in providing near normalization of most plasma protein concentrations in a Factor I deficient patient. However, the preparation was not virus inactivated.

Treatment with plasma infusions has likewise been found effective, cf. D. J. Barret et al., J. Pediatri. (1984) 104(1), 76, V. Wahn et al., Allergol. Immunopathol. (1980) 8(4), 422 as well as V. Wahn et al, J. Clin. Immunol. (1981) 1(4), 228. However, this treatment has some serious drawbacks:

Factor I deficient patients have large amounts of C3 convertase in the blood. C3, administered via the plasma, is therefore immediately cleaved to C3a and C3b, as described above. C3a, which is an anaphylotoxin, can cause anaphylactic reactions in connection with plasma infusion, cf. V. Wahn et al., J. Pediatr. (1984) 105(4), 673. Further, the resulting C3b, in combination with Factor B, likewise administered with the plasma, has a stimulating effect on the alternative pathway. The presence of the complement components C3 and Factor B in the administered plasma thus weakens the efficacy of Factor I regulation of the alternative pathway. Finally, it is not possible to eliminate the risk of viral transmission by plasma infusions.

Temporary decreased levels of Factor I and Factor H are observed in patient suffering from systemic lupus erythematosus (SLE). Kaneko (EP 0 222 611) showed that administration of Factor H and/or Factor I to mice suffering from autoimmune diseases resembling those of human SLE, rheumatoid arthritis and glomerulonephritis, were effective in improving or preventing the proteinuria, that represents the pathological conditions of the autoimmune diseases. Kaneko, however, did not submit the Factor I preparation to neither a virus inactivation step nor a specific Factor B depletion step. As essential problem in the therapeutic use of preparations or fractions produced from human blood or blood plasma is that this blood or blood plasma may contain infectious viruses. Examples of such infectious viruses are hepatitis B virus, non-A, non-B hepatitis virus and human immunodeficiency virus. Transmission of infectious viruses is known in general from the use of preparations produced from human blood or blood plasma. Examples of such preparations are coagulation Factor VIII, coagulation Factor IX, coagulation Factor XIII, immunoglobulin and antithrombin III.

Various processes are known for removal of infectious viruses from therapeutic preparations or solutions containing these produced from human blood or blood plasma. Such a known process comprises heating for 10 hours at 60° C. of aqueous solutions containing therapeutic protein, thereby providing safety against transfer of infectious viruses when using preparations containing these plasma proteins. To avoid denaturation or other damage to the therapeutically active protein in the aqueous solution, it is necessary, however, to add stabilizers during the heat treatment.

Thus, salts of fatty acids or amino acids are added as stabilizers in a heat treatment for 10 hours at 60° C. of solutions containing human albumin or protein concentrate, cf. Gellis et al., J. Clin. Invest. (1948), 27, 239. Use of this process for treatment of human albumin or protein concentrate has entailed that since the process was introduced in 1948, no infectious viruses have been transmitted when using these preparations. This process involved no or only insignificant losses of the therapeutic plasma protein albumin.

Solutions containing plasminogen may be stabilized with the amino acid lysine during a heat treatment af 60° C. for 10 hours, cf. Baumgarten et al., US Pat. No. 3 227 626, (1966). This process destroys the presence of hepatitis virus according to the patent.

Solutions containing the coagulation Factor XIII may be heated at 60° C. for 10 hours in the presence of an amino acid, a monosaccharide or a sugar alcohol, cf. Fukuhima, Patent Sho 51-134878, (1976). A loss of Factor XIII activity of about 50% has been reported with this process.

Furthermore, solutions containing the proteinase inhibitor anti-thrombin III may be stabilized with salts of citric acid prior to heating for 10 hours at 60° C., cf. Holleman et al., Throm. & haemo. (1977), 38, 201. The loss of the therapeutic protein antithrombin III amounts to about 30% in this process.

Finally, the DE Offenlegungsschrift 29 16 711 (1980) discloses a process for heat treatment of Factor VIII for 10 hours at 60° C. while reducing a contaminating fibrinogen content. The stabilizer used is a saccharide or a sugar alcohol in combination with a high concentration of amino acid. The amino acid present causes the fibrinogen of the Factor VIII solution to be precipitated. In this process, the Factor VIII solution is admixed with e.g. 50% w/w saccharose and 2M e glycine during the heat treatment.

No methods of producing a virus inactivated Factor I preparation has been described in the literature. However, the present invention provides a process for producing a solution of Factor I essentially free of infectious viruses and Factor B, which is safe against transfer of infectious viruses, the method comprising subjecting a solution containing Factor I, optionally recovered from plasma, to pasteurization by heating to 55° to 65° C. for 0.5 to 100 hours, preferably at 60° C. for 4 to 24 hours, in the presence of one or more stabilizers for Factor I. The heat treatment is more preferably performed at about 60° C. for 5 to 15 hours.

The invention enables production of a Factor I preparation which is practically protected against transmission of active viruses and the complement factor, Factor B, in one step.

If the invention is combined with a fractionation step in which C3 activity is removed, e.g. by PEG precipitation as described in example 1, a preparation will be obtained which has two very important advantages over plasma in the treatment of Factor I deficiency since it is, in practice, free of viruses and is in practice without C3 and Factor B activity, which, as described above, may cause anaphylactic reactions. The product is also superior to the Factor I preparations described by Kaneko (EP 0 222 611) for treatment of autoimmune diseases because these products were not safe with regard to the risk of viral transmission.

Thus, the invention makes it possible to introduce a considerable improvement in the treatment of Factor I deficient patients over the common treatment with plasma infusions. The process with heat treatment for ½ to 100 hours at 55 to 65° C. of a solution containing Factor I with a saccharide and/or a sugar alcohol and/or an amino acid as a stabilizer may be performed on any fraction or preparation containing Factor I.

Solutions containing Factor I are admixed with a saccharide and/or a sugar alcohol and/or an amino acid. The stabilization of Factor I increases with increased addition of saccharide, sugar alcohol or amino acid; thus, addition may be effected until saturation of one or more of these types of stabilizers. Stabilization of Factor B likewise increases with increased addition of saccharide and/or sugar alcohol, but there will be a range for the concentration of these stabilizers where no Factor B is present in the heat treated solutions, and a great yield of Factor I is obtained after heat treatment for 10 hours at 60° C. It is remarkable e.g. that stabilization with 55% (w/w) saccharose results in an occurrence of Factor B of 21% after heat treatment at 60° C. for 10 hours, while the use of 30% (w/w) saccharose gives total denaturation of Factor B already within 4 hours at 60° C. The same distinct effect is not seen for Factor I, cf. example 1, part B and example 3. The use of amino acids as a stabilizer shows no stabilization of Factor B, while a great yield of Factor I can be obtained after heat treatment for 10 hours at 60° C. This fact renders it possible to produce a Factor I preparation which is without Factor B activity.

Removal of saccharide, sugar alcohol or amino acid from the solution containing Factor I after the heat treatment can be effected by ion exchange or dialysis. After removal of the stabilizer, the solution may be concentrated to the desired concentration, e.g. by means of ultrafiltration, following which the preparation may optionally be freeze-dried in order to improve the stability until use when it is reconstituted. Factor I may be determined by rocket immuno electrophoresis with rabbit anti-human-antibody monospecific for Factor I (produced by the Institute of Medical Microbiology at the University of Odense, Denmark). The sample size is 10 µl. The standard is freeze-dried human plasma (KABI).

Factor B may be determined by radial immunodiffusion with rabbit antihuman Factor B antibody (Behring, anti C3 activator). The sample size is 10 µl. The standard is likewise freeze-dried human plasma (KABI).

Since antibody against C3 is not commercially available, presence of C3 can be excluded by the following indirect method, cf. I. Brandslund et al., Scand. J. Clin. Lab. Invest. (1984) 44 suppl. 168, 57: antibodies against the C3 degradation product C3c react with C3 as well as C3c, but not with C3d. Correspondingly, antibodies against C3d react with both C3 and C3d, but not with C3c. The total C3 and C3c activity may be determined by rocket immuno electrophoresis with rabbit anti-human-antibody agonist C3c (Dakopatts). The sample size is 15 µl. The total C3 and C3d concentration can be determined correspondingly by rocket immuno electrophoresis with rabbit anti-human-antibody against C3d (Dakopatts). In both assays, the standard is freeze-dried human plasma (KABI). If just one of these electrophoreses gives a negatige response (no rocket), this means that there is no C3 in the sample.

The concentration of saccharose may be determined by iodometric titration according to a method, modified with respect to the one described in Ph. Nord. 63 Vol. II, page 558. The process of the invention is illustrated by the following examples.

EXAMPLE 1

Part A

Fresh frozen plasma is thawed and PEG (18.5%) is added. The precipitate is centrifuged off. Then pH is adjusted to 4.8, so that most of the proteins are precipitated. The precipitate is centrifuged off and redissolved in water until 86% of the original plasma volume. This solution contains:

| | |
|---|---|
| Factor I: | 0.6 U/ml |
| Factor B: | 0.3 U/ml |
| C3: | 0 U/ml |

Further, 0.3 U C3d/ml is present, but no C3c since all C3 and C3c activity is precipitated in the first precipitate.

Part B

The starting material is an aqueous solution containing 0.4 U of Factor I/ml and 0.16 U Factor B/ml, produced according to the method described in part A. In the solution, pH is adjusted to 7.0, and 5 g of solution are weighed in each of 8 vials. The vials are placed in water bath at 37° C. for 6 minutes. 0–55% (w/w) saccharose is added to each vial, cf. the table below. After dissolution of the saccharose, pH is again adjusted to 7.0. Then the vials are sealed and heat treated for 10 hours at 60° C. Factor I and Factor B are determined by rocket immuno electrophoresis and radial immuno electrophoresis, respectively, both in heat-treated and non-heat-treated, formulated samples.

| % (w/w) saccharose in the formulated solution | % recovery of Factor I activity | % recovery of Factor B activity |
| --- | --- | --- |
| 0 | 0 | 0 |
| 25 | 69 | 0 |
| 30 | 80 | 0 |
| 35 | 94 | 6 |
| 40 | 87 | 11 |
| 45 | 100 | 13 |
| 50 | 92 | 15 |
| 55 | 89 | 21 |

Part C

The aqueous heat treated solution formulated with 30% (w/w) saccharose, as described in part B, is the starting material. pH is adjusted to 7.8. The solution is applied to a column packed with DEAE Sepharose FF (Pharmacia) ion exchange gel, equilibrated in phosphate buffer having a conductivity of 2.0 mS and pH 7.8. After application of the sample to the gel, it is flushed with 1.5 column volumes of equilibration buffer, followed by elution with a phosphate buffer having a conductivity of 4.0 mS and pH 7.8. The eluate is collected. Both Factor I activity (rocket immune electrophoresis) and saccharose concentration (ionometric titration) are determined in the starting sample for ion exchange as well as eluate.

The recoveries of Factor I and saccharose are 64% and 1.1%, respectively.

The eluate is concentrated by means of ultrafiltration and is freeze-dried.

EXAMPLE 2

The starting material is an aqueous solution containing 0.6 U Factor I/ml and 0.3 U Factor B/ml, cf. example 1, part A. In the solution, pH is adjusted to 7.0, and 5 g of solution are weighed in each of 13 vials. 0–50% (w/w) sorbitol or 0.5–1.8M lysine or 0.5–2.0M glycine are added to the vials, cf. the following table. After dissolution of the stabilizer, pH is adjusted again to 7.0. Then the vials are sealed and heat treated for 10 hours at 60° C. Factor I and Factor B are determined by rocket immuno electrophoresis and radial immunodiffusion, respectively, both in heat-treated and non-heat-treated samples.

| Amount of stabilizer in the formulated solution | % recovery of Factor I activity | % recovery of Factor B |
| --- | --- | --- |
| 0 | 0 | 0 |
| 5% (w/w) sorbitol | 21 | 0 |
| 10% (w/w) sorbitol | 59 | 0 |
| 15% (w/w) sorbitol | 75 | 0 |
| 20% (w/w) sorbitol | 85 | 0 |
| 30% (w/w) sorbitol | 93 | approx. 3 |
| 40% (w/w) sorbitol | 96 | 5 |
| 50% (w/w) sorbitol | 100 | 8 |
| 0.5 M lysine | 100 | 0 |
| 1.0 M lysine | 100 | 0 |
| 0.5 M glycine | 0 | 0 |
| 1.0 M glycine | 9 | 0 |
| 2.0 M glycine | 59 | 0 |

EXAMPLE 3

The starting material is an aqueous solution containing 0.63 U Factor I/ml and 0.30 U Factor B/ml, produced as described in example 1 part A. In the solution, pH is adjusted to 7.0, and 30% (w/w) saccharose is added. The formulated solution is distributed in vials so that ½ ml is added in each. The vials are sealed and placed at 60° C. At different times, cf. the following table, vials are moved from storage at 60° C. to −20° C. Solutions are analysed for Factor I activity and Factor B activity by rocket immuno electrophoresis and radial immunodiffusion, respectively.

| Number of minutes at 60° C. | % recovery of Factor I activity | % recovery of Factor B activity |
| --- | --- | --- |
| 0 | 100 | 100 |
| 30 | 100 | 6 |
| 60 | 100 | 4 |
| 120 | 100 | 3 |
| 240 | 92 | 0 |
| 420 | 84 | 0 |
| 600 | 78 | 0 |
| 4446 | 46 | 0 |

We claim:

1. A process for obtaining a solution of plasma-derived C3b inactivator essentially free of Factor B activity and infectious virus activity comprising subjecting a plasma fraction containing C3b inactivator to pasteurization by heating the plasma fraction to about 55°–65° C. for about 0.5–100 hours in the presence of at least one stabilizer selected from the group consisting of a saccharide, a sugar alcohol, and an amino acid, in which said stabilizer is present in an amount sufficient to stabilize C3b inactivator activity and in an amount to effect no more than 10% recovery of Factor B activity.

2. The process of claim 1 in which the plasma fraction is heated to about 60° C. for about 4–24 hours.

3. The process of claim 2 in which the plasma fraction is heated for about 5–15 hours.

4. A solution of plasma-derived C3b Inactivator essentially free of Factor B activity and infectious virus obtained by the process of claim 1.

* * * * *